United States Patent [19]

Wittkampf et al.

[11] Patent Number: 4,549,548
[45] Date of Patent: Oct. 29, 1985

[54] PACEMAKER SYSTEM WITH AUTOMATIC EVENT-PROGRAMMED SWITCHING BETWEEN UNIPOLAR AND BIPOLAR OPERATION

[75] Inventors: Frederik H. M. Wittkampf, Brummen; Willem Boute, Doesburg, both of Netherlands

[73] Assignee: Vitafin N.V., Curacao, Netherlands

[21] Appl. No.: 532,184

[22] Filed: Sep. 14, 1983

[51] Int. Cl.[4] .............................................. A61N 1/36
[52] U.S. Cl. ............................................... 128/419 PG
[58] Field of Search .................................. 128/419 PG

[56] References Cited

U.S. PATENT DOCUMENTS

| | | | |
|---|---|---|---|
| 3,825,015 | 7/1974 | Berkovits | 128/419 D |
| 3,920,024 | 11/1975 | Bowers | 128/419 PG |
| 4,228,303 | 10/1980 | Rickards | 128/419 PG |
| 4,402,322 | 9/1983 | Duggan | 128/419 PG |
| 4,424,812 | 1/1984 | Lesnick | 128/419 PG |

FOREIGN PATENT DOCUMENTS

| | | | |
|---|---|---|---|
| 30897 | 6/1981 | European Pat. Off. | 128/419 PG |
| 2026870 | 2/1980 | United Kingdom | 128/419 PG |

OTHER PUBLICATIONS

"Bipolar Versus Unipolar Issues in DDD Pacing"; Ross G. Baker, Jr. and Eric N. Falkenberg, Nov.–Dec. 1984, Pace, Part II, vol. 7, pp. 1178–1182.
"Long-Term Comparison of Unipolar and Bipolar Pacing and Sensing Using a New Multiprogrammable Pacemaker System", Pace, vol. 6, May–Jun. 1983, Part I.

*Primary Examiner*—William E. Kamm
*Attorney, Agent, or Firm*—Woodcock Washburn Kurtz Mackiewicz & Norris

[57] ABSTRACT

A pacemaker system incorporates an implantable pacemaker and a plurality of electrodes, electrodes preferably being on a pacing lead for a single chamber pacemaker, or a pair of such leads for a dual chamber pacemaker. Programmable connection means are provided for connecting the pacemaker output to a selected combination of lead electrodes, the selection being changed during each pacer cycle to optimize the choice of unipolar and bipolar operation for given pacemaker events. In one mode, the system employs bipolar QRS sensing and unipolar pacing and T-wave sensing. In another mode, the system employs bipolar QRS sensing and pacing, and unipolar T-wave sensing.

15 Claims, 6 Drawing Figures

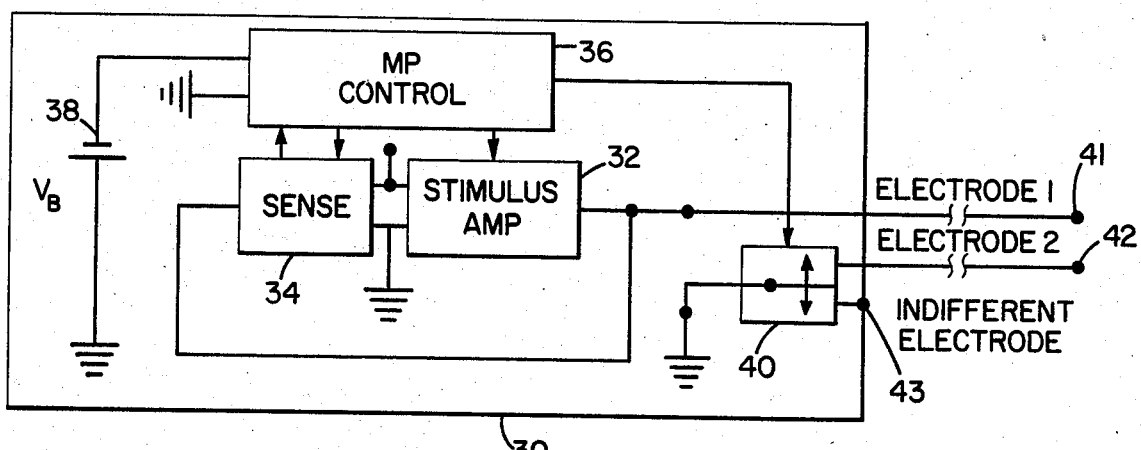
FIG. IA
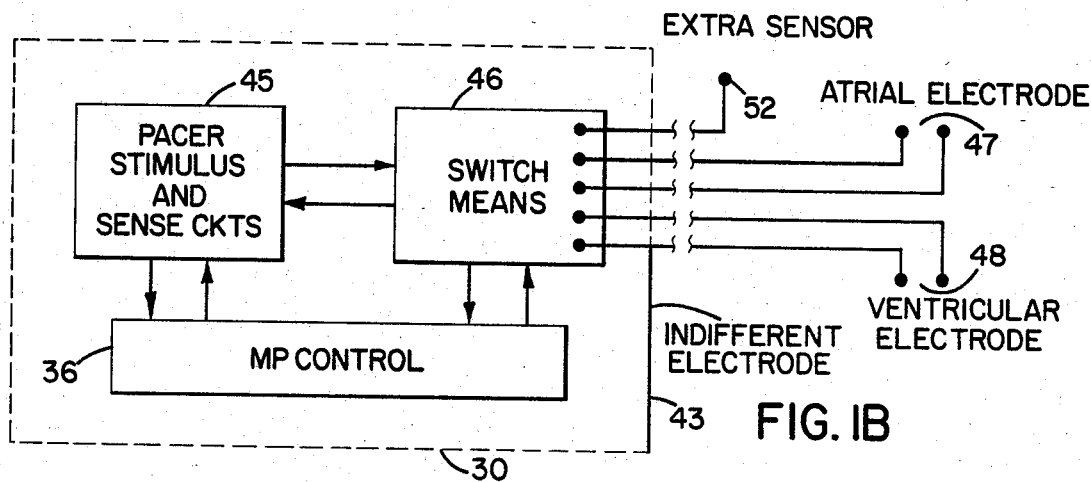
FIG. IB
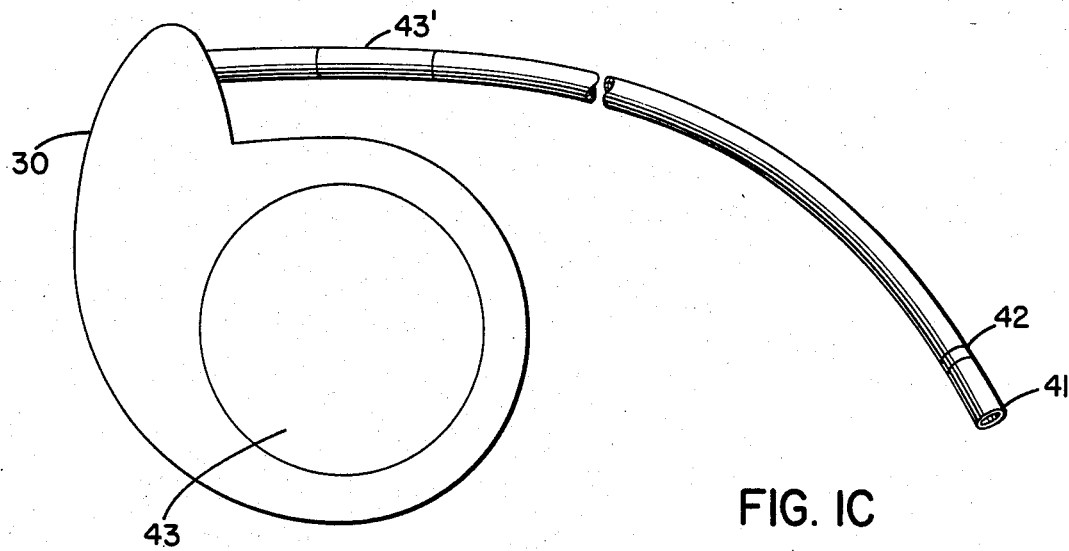
FIG. IC

PACEMAKER SYSTEM WITH AUTOMATIC EVENT-PROGRAMMED SWITCHING BETWEEN UNIPOLAR AND BIPOLAR OPERATION

BACKGROUND OF THE INVENTION

This invention lies in the area of cardiac pacers and the method of operation of same, with programmed means for varying pacemaker operation and, in particular, pacemaker systems and other implantable systems with microprocessor control for switching between unipolar and bipolar operation in accordance with programmed events such as sensing of patient signals and stimulus delivery.

In the field of cardiac pacemakers, there is a need to provide an efficient electrode system for the operations of delivery of stimulus pulses and sensing patient heartbeat signals. In a conventional single chamber demand pacemaker, of the demand type, the electrode system must provide for efficient delivery of ventricular stimulus signals, and also provide efficient pick up of natural QRS signals. In dual chamber pacemakers, there is additionally a need to be able to sense atrial signals, and to deliver atrial stimulus pulses from the pacemaker. In another type of pacemaker, as set forth in U.S. Pat. No. 4,228,803, assigned to the same assignee, there is a need to sense T-waves.

Generally there are two types of electrode systems which are used in cardiac pacing. In the bipolar system of operation, two electrodes are positioned near the tip of a lead which is placed into the heart, the electrodes typically being rings which conduct the stimulus pulse and sense natural cardiac signals. In a unipolar electrode arrangement, a single electrode is placed on the lead, preferably out or near the tip, and an indifferent electrode is utilized at a location remote from the electrode tip. Most typically, in unipolar, or monopolar arrangements, the indifferent electrode is a portion of the pacemaker housing, which is a convenient way of obtaining a large surface indifferent electrode. Alternately, the indifferent electrode may be positioned on the lead itself, at a point proximal to the tip, as is known in the art.

The pacemaker industry has not resolved, and indeed cannot resolve the question of whether unipolar or bipolar operation is generally preferrable. Some physicians adhere to one or the other modes of operation, having their own reasons for doing so. Most pacemaker manufacturers have provided pacing systems for operation in each of the modes, such that the physician can choose a unipolar or a bipolar system. Bipolar leads and systems have the advantages of reduced pick up of electromagnetic interference, and they avoid the problem of unipolar systems wherein the pectoral muscle can be inadvertantly excited. Unipolar systems are generally recognized to have the advantage of better sensitivity for sensing heart signals, and to have reduced polarization problems due to the relatively large indifferent electrode and the relatively small lead electrode. In special applications, such as searching for an evoked response signal (QRS wave) following delivery of a stimulus pulse, or in measuring T-waves, the unipolar system is definitely preferable. There could be a problem if, in a bipolar system, the heart muscle is captured at both electrodes, in which case the sensed T-wave and QRS wave would be simply the difference of the two signals and would be very small.

In view of the above, it is seen that there is a need to provide increased flexibility, by which the pacer system can utilize the advantages of each of the bipolar and unipolar modes of operation for the particular events that are taking place. Thus, there is a need for a system which automatically switches between unipolar and bipolar forms of operation, the switching being programmed for optimal operation of the different pacer events which take place during each pacing cycle. The desirability for switching applies to both single chamber and dual chamber pacing systems. In dual chamber systems, it may be desirable, for example, to have bipolar operation in the atrium to reduce the need for blanking following delivery of the ventricular stimulus, while at the same time having a unipolar electrode arrangement for sensing P waves. Generally, considerations for unipolar and bipolar sensing vary at different times in the pacing cycle, dependent upon the next anticipated event.

While this invention is described in terms of switching between unipolar and bipolar operation in a pacemaker system, it is to be understood that it generally applies to optimized switching of various electrode systems, for pacemakers and other types of devices for delivering stimuli to a patient and/or sensing patient signals. For example, electrode configurations may be used which are not termed unipolar or bipolar, as those terms are understood in the pacemaker art, but which electrode configurations are changed during cycles of operation of the system.

SUMMARY OF THE INVENTION

It is an object of this invention to provide a stimulus delivery system having an implantable device and an electrode configuration with a plurality of electrodes, and a controllable connection circuit for connecting the electrodes to the stimulus/device in various configurations, the circuit being switchable during each device cycle so as to optimize the electrode configuration in terms of system events.

It is another object of this invention to provide a pacing system with microprocessor control for changing the system operation between unipolar and bipolar operation within each pacing cycle, in accordance with programmed events.

It is another object of this invention to provide an implantable device system with programmed means for automatically changing the electrode configuration in accordance with the programmed system operation.

It is a further object of this invention to provide a pacemaker system with program means for cyclically switching the pacemaker sensing means and electrode configuration, to optimize sensing of patient cardiac signals.

It is a further object of this invention to provide a pacemaker system with means for automatically accumulating data corresponding to system operation, and for automatically switching the system electrode configuration in accordance with such accumulated patient data.

In accordance with the above objects, there is provided a pacemaker system having an implantable pacemaker with means for delivering stimulus pulses and means for sensin patient signals, the pacemaker being in programmable connection with an electrode configuration having a plurality of electrodes, and controllable means for switching the electrodes connected to the pacemaker so as to provide alternately unipolar and bipolar operation. The pacemaker system preferably contains microprocessor control for cyclically programming switching between unipolar and bipolar operation to optimize the electrode configuration for predetermined pacing events such as stimulus delivery and sensing of given patient heart signals. In another embodiment, the pacemaker monitors one or more system events over one or more pacemaker cycles, and automatically selects an optimum electrode configuration.

BRIEF DESCRIPTION OF THE DRAWINGS

FIG. 1A is a block diagram showing the main components of a demand pacemaker system in accordance with this invention.

FIG. 1B is a block diagram showing the main components of a dual chamber pacemaker in accordance with this invention.

FIG. 1C is a schematic illustration of a pacemaker and lead, illustrating placement of electrodes to achieve bipolar and unipolar modes of operation.

DESCRIPTION OF THE PREFERRED EMBODIMENT

Figure 2A:
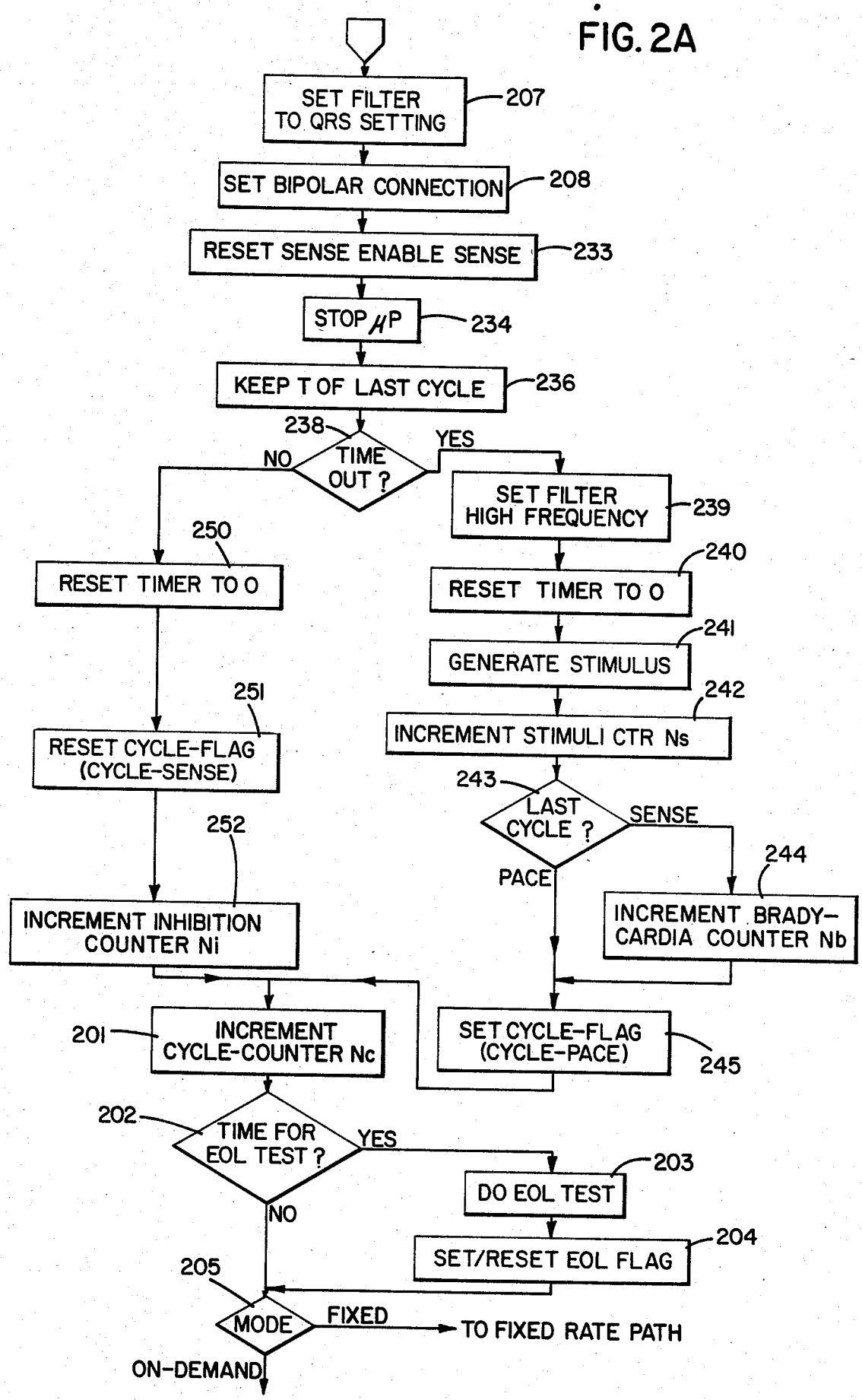
FIGS. 2A and 2B present a flow diagram of a programmable pacemaker utilizing the subject invention.

Referring now to FIG. 1A, a pacemaker is shown in a casing, or housing 30. An indifferent electrode 43, as also shown in FIG. 1C, forms a portion of the outside surface of the casing, as is conventional in the pacemaker art. The pacemaker contains circuitry, as shown at block 32, for generating and delivering stimulus pulses, or stimulus signals, and circuitry as shown at block 34 for sensing patient heart signals, e.g. QRS and T waves, or atrial P waves. A microprocessor control, incorporating a microprocessor chip or chips as well as associated control circuitry, is shown at block 36. Communications as indicated between the microprocessor control and the stimulus and sense circuitry enable overall control of the pacer, in a known manner. A power source as shown at 38 provides a voltage $V_B$ which is applied to all of the circuitry. As illustrated, the negative side of the power source is connected to the circuitry, and the positive side is connected to the system ground. All of these features are conventional and well known in the art. See, for example, European Patent Application No. 81108940.8.

The output of the stimulus amplifier circuitry, as well as the input to the sense circuitry are tied in common and fed through the pacer housing and connected through a conventional lead to a first electrode 41, designated electrode 1 in FIG. 1A. This electrode is typically located at the end of the lead, as illustrated in FIG. 1C. A bipolar lead of conventional design carries a second electrode, suitably a ring positioned proximally to the distal first electrode, and electrically connected by a conductor running the length of the lead. A third electrode is suitably provided by a plate 43 which forms a portion or substantially all of the pacemaker can, or housing, as also illustrated in FIG. 1C.

In the system of this invention, an electronically controlled switch 40 is provided which operates to switch either the second electrode or the indifferent electrode to the system ground. When the switch connects the second electrode (42) to system ground, then the two ring electrodes as seen in FIG. 1C are connected to the pacemaker, and bipolar system operation is achieved. With this mode of connection, a stimulus pulse may be delivered with the voltage difference being directly across the two ring electrodes 41, 42. When the switch 40 is switched so that the indifferent electrode 43 is connected to system ground, then ring electrode 42 is not connected to the pacemaker, and unipolar operation is achieved. In unipolar operation, a delivered stimulus pulse presents a voltage between the small electrode 41 at the tip of the lead, and the large electrode 43 on the pacemaker casing. As is known in the art, the indifferent electrode may be positioned other than on the pacemaker housing, and could be positioned as shown at 43' in FIG. 1C, far proximal on the lead itself.

Figure 2B:
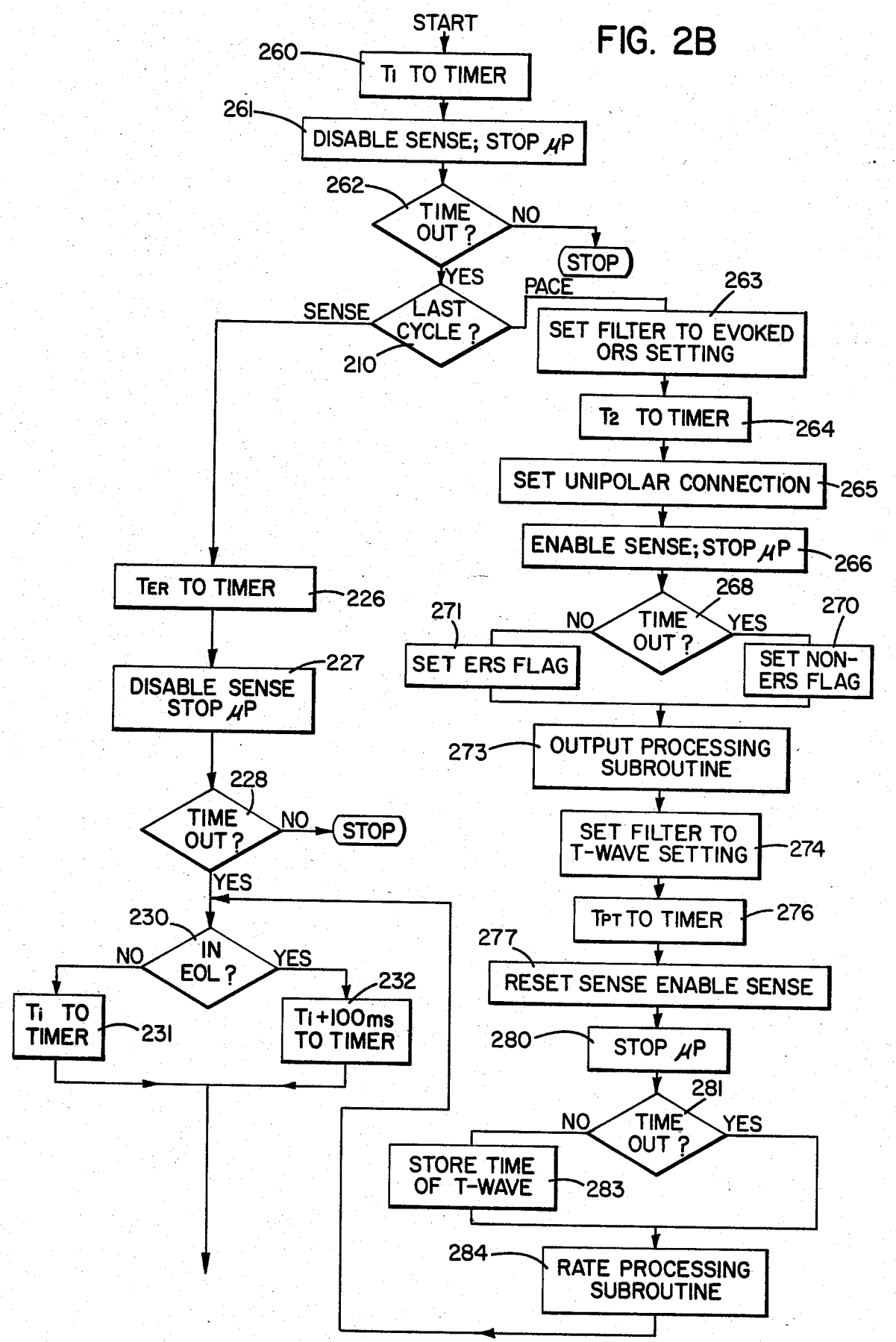

The operation of switch 40, as illustrated in FIG. 1A, is under control of the microprocessor control circuitry 36. Switch 40 may be any well known semiconductor switch, such as is easily provided in the art, the switching operation being under the control of a conventional microprocessor or other analog or digital controller. In the preferred embodiment of microprocessor control, the switch may be accurately controlled at programmed intervals of each pacing cycle, as illustrated in FIGS. 2A and 2B below. It is to be understood that the switch control may take any conventional design form, including the use of analog circuitry in a well known manner.

Referring to FIG. 1B, there is shown a block diagram illustrating a more general system encompassed by this invention, as applied as a dual chamber pacemaker. Microprocessor control circuitry 36 is shown in two-way communication with pacer stimulus and sense circuits as shown in block 45, and switch means as shown in block 46. The switch means provide the function of connecting a plurality of electrodes, in different combinations, to the pacer stimulus and sense circuits. As illustrated, five electrodes may be used, two atrial electrodes 47, two ventricular electrodes 48, and an indifferent electrode 43. It is to be understood that in the general application of this invention, for pacemaker systems or other similar implantable systems, the number of electrodes that may be utilized is unlimited. The invention covers the automatic switching of different electrode configurations during repetitive cycles, the electrode configurations being chosen for use with one or more predetermined programmed events. In the pacemaker system embodiment, the programmed events include sensing of different natural and/or evoked heart signals, and delivery of stimulus pulses to one or more heart locations. As illustrated in FIG. 1B, the switch means may also controllably connect to an extra sensor 52, which may be an additional cardiac electrode or a sensor for sensing another patient parameter.

Referring now to FIGS. 2A and 2B, there is illustrated a flow diagram covering a cycle of pacer operation. The flow diagram is repeated continuously each pacer cycle.

Referring to FIG. 2A, there is illustrated an example of a microprocessor controlled cardiac pacemaker system which changes its electrode configuration, as well as filter characteristics, within the pacer cycle. The program, as illustrated, is for a ventricular demand pacer, and starts at a time just after the time out of the pacer refractory period. At block 207, the filter of the input amplifier, connected to receive a patient cardiac signal, is set to an appropriate QRS setting, i.e., set to an appropriate bandpass for detecting a patient QRS signal. At block 208, a bipolar connection is set, for bipolar QRS sensing. At block 233, the microprocessor enables sensing through the input amplifier, and, for example, sets the sensitivity at 2 mV. At block 234, the microprocessor is stopped to await either timeout or a sensed QRS. When either of these events occurs, the microprocessor picks up at block 236 and records the time T of the last cycle, and then determines whether a timeout has occurred, at block 238.

If a timeout has occurred, meaning there has been no natural patient beat, the program block branches to the right. In preparation for generating the stimulus, the filter of the input amplifier is first set to a high frequency characteristic, at block 239, in order to quickly damp out any artifacts produced by the generated stimulus. If unipolar pacing is desired, a unipolar connection is also set at this point. Thereafter the pacer timer is set to zero at block 240, and the stimulus is generated at block 241. Bookkeeping type operations are done at 242-245 and 201; an end-of-life (EOL) test may be done at 202-204, and at 205 the program exits either to the "on-demand" path of FIG. 2B, or to a fixed rate path. If the "NO" branch is taken at block 238, no stimulus is generated, and bookkeeping functions 250-252 are carried out.

Referring to FIG. 2B, the program continues after the stimulus delivery provided in FIG. 2A. The program as illustrated provides for controlling the rate of delivered stimulus pulses as a function of stimulus T time intervals. A time delay is introduced at block 260, corresponding to the delay between the stimulus and the start of evoked response sensing. The sense amplifier is disabled at block 261, and the microprocessor is stopped to wait for the delay $T_1$. At block 262, the microprocessor determines whether the timer has timed out. If yes, and the last cycle was a pace cycle, as determined at 210, the pacer control branches to the right. At block 263, a switchable filter such as disclosed in U.S. application Ser. No. 475,024 is set to the evoked QRS setting, i.e., to a filter characteristic optimally designed to detect an evoked QRS. A period T2 is put into the timer at 264, during which the pacer looks for the evoked response. At block 265, the electrodes are connected for unipolar operation, e.g., switch 40 is set to connect the indifferent electrode to ground, leaving ring electrode 42 unconnected. The sense amplifier is enabled at block 266, for example with a sensitivity of 8 mV. At block 268, it is determined whether the timer has timed out. If no, meaning that an evoked response was detected, the ERS flag is set at block 271. If yes, meaning that there was no evoked response, the non-ERS flag is set at 270. Following this, at block 273, the microprocessor goes through an output processing subroutine, to change the stimulus magnitude if required to achieve heart capture. At block 274, the filter characteristic of the input amplifier is modified to a characteristic adapted for detecting the T wave portion of the heart signal. Following this, at block 276, a time interval TPT corresponding to the T wave time is set into the timer, and at block 277 the sense amplifier is enabled at a sensitivity of, for example, 1 mV. The microprocessor is stopped at 280, and is started again at 281 either by a sensed T wave or by timing out. If it is not timed out, meaning that a T wave was sensed, the time of this T wave in relation of the delivered pulse stimulus is stored at 283. At block 284, the microprocessor goes through a rate subprocessing routine to change the pacer rate, as set forth in U.S. Pat. No. 4,228,803. If, at block 210, it is determined that the last cycle was ended by a sensed natural QRS, the program branches to block 226, where the refractory interval is established by setting the timer to Ter. The sense amplifier is disabled at block 277, and the microprocessor is stopped to await the time out of the refractory period as shown at block 228.

As illustrated, FIGS. 2A and 2B show an example of cyclic bipolar operation for sensing QRS and for stimulation, and monopolar (unipolar) T wave sensing. Unipolar pacing can be achieved by setting the unipolar connection after QRS sensing (or time out) and before delivery of the stimulus pulse. Dual chamber operation employs additional such switching steps in accordance with desired electrode modes for atrial sensing and stimulating.

Figure 3:
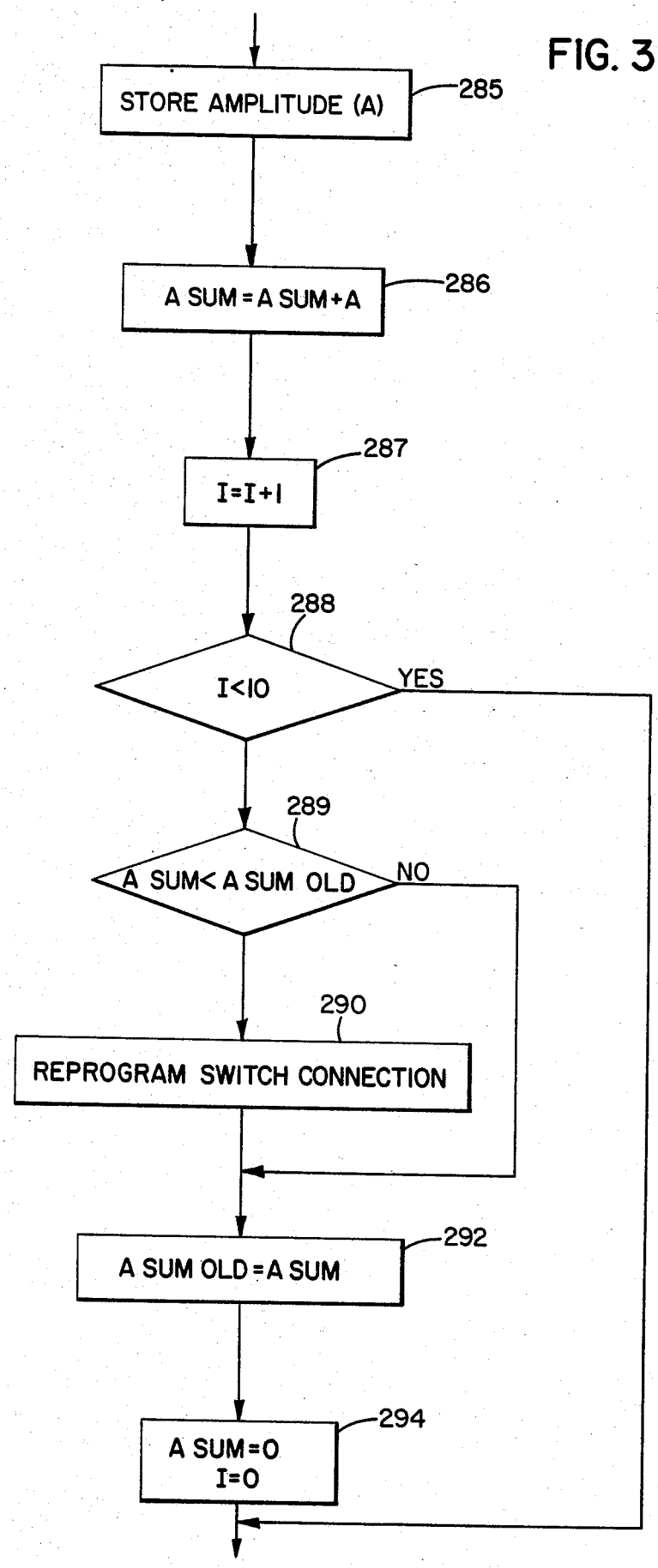
FIG. 3 is a flow diagram of a routine for switching the electrode configuration as a function of performance monitored over a plurality of cycles of operation.

Referring to FIG. 3, there is illustrated a routine which can be utilized in a pacemaker or other implantable device, for monitoring performance and reprogramming a desired switch connection as a function of monitored performance. The reprogramming can be done with respect to cyclical switching, e.g., for the embodiment of FIGS. 2A and 2B periodic signal sensing can be changed from bipolar to unipolar, or vice versa. Alternately, the reprogramming can be done on a permanent or fixed basis, e.g., the pacemaker may switch from fixed unipolar operation to fixed bipolar, or vice versa.

The program of FIG. 3 illustrates monitoring a sensed heartbeat signal to obtain a measure of whether the sensing operation would be performed better in the unipolar or bipolar mode. The amplitude of a received input signal, e.g. QRS or P wave, is stored at block 285. At block 286, a new sum designated A SUM is accumulated by adding the just received amplitude A to the prior sum. At block 287, the number of iterations I is incremented by 1. In the illustration, the routine iterates 10 times in order to accumulate a sum, but it is to be understood that one or more measurements can be made, and that the number of iterations is a matter of choice. At block 288, it is determined whether I is less than 10. If yes, more cycles are to be measured, and the routine branches directly to the end. If no, meaning that 10 measurements have now been accumulated, the program proceeds to block 289 where it is determined whether A SUM is less than the prior, or old A SUM. If no, meaning that A SUM has increased, reflecting improved performance, the routine branches to block 292. If yes, meaning that performance has deteriorated, the routine first performs the operation at block 290 of changing the switch connection, i.e., changing the electrode mode for the sensing activity from bipolar to unipolar, or vice versa. Thereafter, at block 292, the microprocessor stores the accumulated A SUM as A SUM OLD. At block 294, the present values of A SUM and I are set to zero, and the program exists.

The subroutine of FIG. 3 may be run continuously initiated periodically by a counter in the pacemaker; or initiated by an external program signal. It is presented as an illustration of utilizing device-accumulated information to make the choice of mode setting. While the illustration given relates to sensing a received heart signal, patient information relative to stimulus delivery can likewise be accumulated. With evoked response sensing, a patient threshold can be determined by known means, and threshold compared for unipolar versus bipolar stimulus delivery. It is to be understood that the routine for cyclic switching between unipolar and bipolar operation can be re-programmed from an external source, by means well known in the art.

We claim:

1. Pacemaker apparatus having an implantable pacemaker, said pacemaker having stimulus means for generating stimulus pulses, sensing means for sensing heart signals, and cyclic means for controlling said pacemaker to carry out cyclic operation, a lead with at least two spaced lead electrodes thereon, and an indifferent electrode, comprising:
   connection means for controllably connecting said sensing means and said stimulus means to respective selected ones of a plurality of combinations of said lead electrodes and said indifferent electrode;
   selection means for selecting respective first and second ones of said combinations for sensing of respective heart signals at different times during a cycle of pacemaker operation; and
   control means for controlling said connection means in accordance with said selected combinations 2. The apparatus as described in claim 1, wherein a first of said combinations comprises one of said lead electrodes and said indifferent electrode, and a second of said combinations comprises two of said lead electrodes, thereby providing selection between unipolar and bipolar operation.

3. The apparatus as described in claim 2, wherein said pacemaker is housed in a housing, said housing having at least a portion of the outside of which comprises said indifferent electrode.

4. The apparatus as described in claim 1, said sensing means having first sensing means for sensing a first selected heartbeat signal and second sensing means for sensing a second selected heartbeat signal, and wherein said selection means has first selection means for selecting said unipolar connection for sensing of said first selected heartbeat signal once each pacing cycle, and second selection means for selecting said bipolar connection for sensing of said second selected heartbeat signal once each cycle.

5. The apparatus as described in claim 4, wherein said first sensing means senses T waves.

6. The apparatus as described in claim 5, wherein said second sensing means senses QRS signals.

7. The apparatus as described in claim 1, said sensing means having QRS means for sensing QRS signals and T wave sensing means for sensing T waves, and wherein said selection means selects said unipolar connection each pacing cycle for T wave sensing and delivery of a stimulus pulse, and selects said bipolar connection each cycle for QRS sensing.

8. The apparatus as described in claim 1, wherein said selection means further comprises means for selecting one of said combinations for delivery of a stimulus pulse during said cycle.

9. Pacemaker apparatus for delivering stimulus pulses, said apparatus having pacing means for generating said stimulus pulses and sensing means for sensing patient heartbeat signals, a housing which houses at least said pacing means, at least a portion of which housing comprises an indifferent electrode, and a lead having at least two electrodes, said pacing means having program means for carrying out cyclical operation, characterized further by
   connecting means for selectively connecting said pacing means to two of said lead electrodes for bipolar operation or to said indifferent electrode and one of said lead electrodes for unipolar operation,
   first control means operable each pacemaker cycle to control said connection means to make a selected connection during delivery of a stimulus pulse, and
   second control means operable twice each pacemaker cycle to control said connection means to make predetermined selected connections for sensing of patient heartbeat signals at two respective times during said each cycle.

10. The apparatus as described in claim 9, wherein said connection means comprises a switching circuit which is controllable to connect said pacing means alternately to one of said lead electrodes or to said indifferent electrode.

11. The apparatus as described in claim 9, further characterized by having a second lead having at least two electrodes and second connection means for connecting said pacing means to said second lead for unipolar or bipolar operation.

12. Pacemaker apparatus for delivering stimulus pulses, said apparatus having pacing means for generating said stimulus pulses and sensing means for sensing patient heartbeat signals, a housing which houses at least said pacing means, at least a portion of which housing comprises an indifferent electrode, and a lead having at least two electrodes, said pacing means having program means for carrying out cyclical operation, characterized further by
   connection means for selectively connecting said pacing means to two of said lead electrodes for bipolar operation or to said indifferent electrode and one of said lead electrodes for unipolar operation,
   monitoring means for monitoring the occurrence and absence of occurrence of at least one said sensed heartbeat signal during each pacemaker cycle, and
   control means for controlling said connection means during each said cycle as a function of said monitoring.

13. The apparatus as described in claim 12, wherein said sensing means has QRS timing means for timing out a QRS period for sensing a QRS signal, said control means controlling said connection means for bipolar operation during said QRS period and for unipolar operation at about the end of said period.

14. Pacemaker apparatus having a pacemaker with program means for controlling repetitive cycles of pacemaker operation and a plurality of electrodes for delivering stimulus pulses and sensing heart activity, said pacemaker comprising:
   connection means for controllably connecting said pacemaker to a selected combination of said electrodes;
   determining means for determining pacemaker data over a plurality of said cycles, and
   control means for controlling said connection means as a function of said determined pacemaker data.

15. The apparatus as described in claim 8, wherein said determining means comprises means for cyclically sensing heart signals and for generating values representative of a feature of said sensed signals, means for accumulating said values over a predetermined number of cycles to derive summation values, and means for comparing respective summation values.

* * * * *

UNITED STATES PATENT AND TRADEMARK OFFICE
CERTIFICATE OF CORRECTION

PATENT NO. : 4,549,548

DATED : October 29, 1985

INVENTOR(S) : Frederik H.M. Wittkampf; Willem Boute

It is certified that error appears in the above-identified patent and that said Letters Patent is hereby corrected as shown below:

In Column 2, Line 64, the word "sensin" should be --sensing--.

Signed and Sealed this

Eighteenth Day of February 1986

[SEAL]

Attest:

DONALD J. QUIGG

Attesting Officer

Commissioner of Patents and Trademarks